(12) United States Patent
Kallesøe Nielsen et al.

(10) Patent No.: US 8,394,060 B2
(45) Date of Patent: Mar. 12, 2013

(54) VENTED DRUG RESERVOIR UNIT

(75) Inventors: Karsten Kallesøe Nielsen, Glostrup (DK); Lars Aagaard, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 55 days.

(21) Appl. No.: 13/046,070

(22) Filed: Mar. 11, 2011

(65) Prior Publication Data

US 2011/0160670 A1 Jun. 30, 2011

Related U.S. Application Data

(63) Continuation of application No. 12/090,499, filed as application No. PCT/EP2006/067483 on Oct. 17, 2006.

(60) Provisional application No. 60/727,467, filed on Oct. 17, 2005.

(30) Foreign Application Priority Data

Oct. 17, 2005 (EP) ..................... 05109630

(51) Int. Cl.
*A61M 1/00* (2006.01)

(52) U.S. Cl. ........................ 604/118; 604/324

(58) Field of Classification Search .............. 92/81, 142; 96/184; 128/200.21; 137/2, 179, 848; 220/368; 222/69; 604/118, 129, 140, 151, 324
See application file for complete search history.

(56) References Cited

U.S. PATENT DOCUMENTS

| | | |
|---|---|---|
| 2,605,765 A | 8/1952 | Kollsman |
| 4,077,405 A | 3/1978 | Haerten et al. |
| 4,140,117 A | 2/1979 | Buckles et al. |
| 4,201,207 A | 5/1980 | Buckles et al. |
| 4,340,048 A | 7/1982 | Eckenhoff |
| 4,552,561 A | 11/1985 | Eckenhoff et al. |
| 4,562,751 A | 1/1986 | Nason et al. |
| 4,685,903 A | 8/1987 | Cable et al. |
| 4,811,845 A | 3/1989 | Baggett |
| 4,898,582 A * | 2/1990 | Faste .............................. 604/141 |
| 5,169,390 A | 12/1992 | Athayde et al. |

(Continued)

FOREIGN PATENT DOCUMENTS

| | | |
|---|---|---|
| DE | 2552446 | 5/1977 |
| DE | 4120267 | 12/1992 |

(Continued)

OTHER PUBLICATIONS

Non-Final Office Action Mailed Dec. 19, 2008 for U.S. Appl. No. 11/411,081, filed Apr. 25, 2006; First Named Inventor: Ole Christian Nielsen.

(Continued)

*Primary Examiner* — Nicholas Lucchesi
*Assistant Examiner* — Gerald Landry, II
(74) *Attorney, Agent, or Firm* — Wesley A. Nicolas; Marc A. Began; Reza Green

(57) ABSTRACT

A reservoir unit is provided comprising a housing in which a reservoir with a transparent portion is arranged, the housing comprising a window allowing a portion of the reservoir to be inspected. The reservoir unit is adapted to be moved from a first "cold" condition to a second "warm" condition with no visible water condensing on the interior surface of the window portion. Further, the vent is adapted to provide pressure equalization between the interior of the housing and the exterior. In this way it is possible to perform visual inspection of the reservoir at all times without being confused by dew or condensed water drops, e.g. when a prefilled reservoir unit containing a drug which requires storage at a given low temperature, as is the case for insulin-containing drugs, is taken out in ambient temperature.

1 Claim, 5 Drawing Sheets

U.S. PATENT DOCUMENTS

| | | | |
|---|---|---|---|
| 5,257,980 | A | 11/1993 | Van Antwerp et al. |
| 5,487,738 | A | 1/1996 | Sciulli |
| 5,527,288 | A | 6/1996 | Gross et al. |
| 5,568,806 | A | 10/1996 | Cheney, II et al. |
| 5,616,132 | A | 4/1997 | Newman |
| 5,665,065 | A | 9/1997 | Colman et al. |
| 5,814,020 | A | 9/1998 | Gross |
| 5,858,001 | A | 1/1999 | Tsals et al. |
| 5,896,989 | A | 4/1999 | Ropiak et al. |
| 5,957,895 | A | 9/1999 | Sage et al. |
| 5,997,501 | A | 12/1999 | Gross et al. |
| 6,045,534 | A | 4/2000 | Jacobsen et al. |
| 6,068,613 | A | 5/2000 | Kriesel et al. |
| 6,074,369 | A | 6/2000 | Sage |
| 6,248,093 | B1 | 6/2001 | Moberg |
| 6,251,098 | B1 | 6/2001 | Rake et al. |
| 6,280,148 | B1 | 8/2001 | Zengerle et al. |
| 6,287,289 | B1 | 9/2001 | Niedospial, Jr. |
| 6,290,678 | B1 | 9/2001 | Aydellotte et al. |
| 6,302,869 | B1 | 10/2001 | Klitgaard |
| 6,364,865 | B1 | 4/2002 | Lavi et al. |
| 6,485,471 | B1 | 11/2002 | Zivitz et al. |
| 6,500,150 | B1 | 12/2002 | Gross et al. |
| 6,554,798 | B1 | 4/2003 | Mann et al. |
| 6,589,229 | B1 | 7/2003 | Connelly et al. |
| 6,589,369 | B2 | 7/2003 | Yokio et al. |
| 6,622,037 | B2 | 9/2003 | Kasano |
| 6,764,567 | B2 | 7/2004 | Sperko et al. |
| 6,809,653 | B1 | 10/2004 | Mann et al. |
| 7,250,037 | B2 | 7/2007 | Shermer et al. |
| 2002/0040208 | A1 | 4/2002 | Flaherty et al. |
| 2002/0169416 | A1 | 11/2002 | Gonelli et al. |
| 2002/0169439 | A1 | 11/2002 | Flaherty |
| 2003/0088238 | A1 | 5/2003 | Poulsen et al. |
| 2003/0163090 | A1* | 8/2003 | Blomquist et al. ............ 604/154 |
| 2004/0059316 | A1 | 3/2004 | Smedegaard |
| 2004/0068230 | A1 | 4/2004 | Estes et al. |
| 2004/0092873 | A1 | 5/2004 | Moberg |
| 2004/0122353 | A1 | 6/2004 | Shahmirian et al. |
| 2004/0138612 | A1 | 7/2004 | Shermer et al. |
| 2005/0022274 | A1 | 1/2005 | Campbell et al. |
| 2005/0065760 | A1 | 3/2005 | Murtfeldt et al. |
| 2005/0277884 | A1* | 12/2005 | Kriesel et al. ................. 604/132 |
| 2006/0249687 | A1* | 11/2006 | Chao et al. ............... 250/441.11 |
| 2007/0088268 | A1* | 4/2007 | Edwards ...................... 604/136 |

FOREIGN PATENT DOCUMENTS

| | | |
|---|---|---|
| EP | 1177802 | 2/2002 |
| EP | 1396275 | 3/2004 |
| JP | 2002-529204 | 9/2002 |
| WO | WO92/22338 | 12/1992 |
| WO | WO96/14026 | 5/1996 |
| WO | WO0029049 | 5/2000 |
| WO | WO 02/41999 | 5/2002 |
| WO | WO03/026726 | 4/2003 |
| WO | WO03/037403 | 5/2003 |
| WO | WO2004/056412 | 7/2004 |
| WO | WO2005/002649 | 1/2005 |
| WO | WO2005/011779 | 2/2005 |
| WO | WO 2005/039673 | 5/2005 |
| WO | WO 2005/072795 | 8/2005 |
| WO | WO 2005/077438 | 8/2005 |

OTHER PUBLICATIONS

Notice of Allowance Mailed Jul. 17, 2009 for U.S. Appl. No. 11/411,081, filed Apr. 25, 2006; First Named Inventor: Ole Christian Nielsen.

Notice of Allowance Mailed May 28, 2010 for U.S. Appl. No. 11/411,081, filed Apr. 25, 2006; First Named Inventor: Ole Christian Nielsen.

Notice of Allowance Mailed Aug. 25, 2010 for U.S. Appl. No. 11/411,081, filed Apr. 25, 2006; First Named Inventor: Ole Christian Nielsen.

Non-Final Office Action Mailed Apr. 30, 2010 for U.S. Appl. No. 12/579,169, filed Oct. 14, 2009; First Named Inventor: Ole Christian Nielsen.

Final Office Action Mailed Sep. 14, 2010 for U.S. Appl. No. 12/579,169, filed Oct. 14, 2009; First Named Inventor: Ole Christian Nielsen.

Non-Final Office Action Mailed Apr. 10, 2009 for U.S. Appl. No. 12/066,712, filed Mar. 13, 2008; First Named Inventor: Ole Christian Nielsen.

Non-Final Office Action Mailed Oct. 27, 2009 for U.S. Appl. No. 12/066,712, filed Mar. 13, 2008; First Named Inventor: Ole Christian Nielsen.

Final Office Action Mailed Apr. 28, 2010 for U.S. Appl. No. 12/066,712, filed Mar. 13, 2008; First Named Inventor: Ole Christian Nielsen.

Non-Final Office Action Mailed Jul. 24, 2009 in U.S. Appl. No. 11/911,213, filed Oct. 11, 2007; First Named Inventor: Ole Christian Nielsen.

Non-Final Office Action Mailed Apr. 30, 2010 in U.S. Appl. No. 11/911,213, filed Oct. 11, 2007; First Named Inventor: Ole Christian Nielsen.

Final Office Action Mailed Sep. 2, 2010 in U.S. Appl. No. 11/911,213, filed Oct. 11, 2007; First Named Inventor: Ole Christian Nielsen.

Office Action Issued in Connection With Counterpart Danish Application No. PA 2005 00526 Mailed Jan. 30, 2006 for U.S. Appl. No. 11/911,213, filed Oct. 11, 2007; First Named Inventor: Ole Christian Nielsen.

Google Machine Translation of Office Action Filed in Danish Application PA 2005 00526 Mailed Jan. 30, 2006.

International Search Report and Written Opinion Issued in Connection With Counterpart International Application No. PCT/EP2006/061444 Mailed Aug. 9, 2006 for U.S. Appl. No. 11/911,213, filed Oct. 11, 2007; First Named Inventor: Ole Christian Nielsen.

International Preliminary Examination Report Issued in Connection With Counterpart International Application No. PCT/EP2006/061444 Mailed Oct. 25, 2007 for U.S. Appl. No. 11/911,213, filed Oct. 11, 2007; First Named Inventor: Ole Christian Nielsen.

English Abstract of DE 4120267.

English Abstract of JP2002-592204 Filed Sep. 10, 2002.

Google Machine Translation of DE 2552446.

* cited by examiner

VENTED DRUG RESERVOIR UNIT

CROSS-REFERENCE TO RELATED APPLICATIONS

This application is a continuation of U.S. application Ser. No. 12/090,499, filed Apr. 17, 2008 (Allowed), which is a 35 U.S.C. §371 national stage application of International Patent Application PCT/EP2006/067483 (published as WO 2007/045644), filed Oct. 17, 2006, which claimed priority of European Patent Application 05109630.3, filed Oct. 17, 2005; this application further claims priority under 35 U.S.C. §119 of U.S. Provisional Application 60/727,467, filed Oct. 17, 2005.

The present invention generally relates to a reservoir unit containing a fluid drug, the reservoir unit comprising means allowing a condition of the drug to be checked for, for example, but not restricted to, fibrillation of insulin.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. The delivery device may be adapted for discrete use, i.e. injection of an amount of a drug a given number of times during the day, or they may be adapted for continuous or quasi-continuous delivery of drug through a permanent fluid connection between the delivery device and the patient. The former type of device is often referred to as a pen device and the latter type is often termed an infusion pump. A "pen" is typically a mechanical pen-formed device, however, it may have any desirable configuration just as it may comprise a motor for assisted injection of drug.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals. Examples of this type of pump are shown in U.S. Pat. Nos. 4,562,751 and 4,685,903 hereby incorporated by reference. In order to provide a safe, user friendly and robust pump, most pumps are provided with a vent mechanism allowing the pump to accommodate pressure variations (e.g. due to moving interior parts, out-gassing from batteries or variation in ambient pressure), the vent being adapted to provide a certain degree of protection against the entry of water, see e.g. US 2004/0092873 disclosing an external infusion device comprising a housing having a vent port that permits the passage of air into and out of the housing and inhibits the passage of liquids into the housing through the vent port.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use.

When a fluid drug is supplied to a user, it is important that the user can visually inspect the drug to make sure that the drug is not crystallised or polymerised due to e.g. self association or penetration, or that any other visually detectable change of the drug has occurred, such as oxidation of the active drug. For insulin such visual changes are often referred to as "fibrillation". Even weak degrees of fibrillation can be critical for a patient, as it can potentially cause allergy to insulin and change the time-profile for the insulin.

Having regard to the above-identified prior art devices, it is an object of the present invention to provide a reservoir unit with means aiding a user to check the condition of the drug, e.g. to check insulin for fibrillation, in a safe and reliable way.

DISCLOSURE OF ASPECTS OF THE INVENTION

In the disclosure of the present invention, embodiments and aspects will be described which will address one or more of the above objects or which will address objects apparent from the below disclosure as well as from the description of exemplary embodiments.

Thus, in a first aspect a reservoir unit is provided comprising a housing defining an interior, the housing comprising a transparent window portion having an interior surface, and a vent allowing ambient air and aqueous vapour to pass between the interior of the housing and the exterior. A reservoir is arranged within the interior of the housing, the reservoir defining an interior adapted to contain a fluid drug, the reservoir comprising a transparent portion allowing a user to inspect at least a portion of the contained drug through the transparent window portion and the trans-parent reservoir portion. The reservoir unit is adapted to be moved from a first stable condition at 5° C. and 0-100% relative humidity (RH), to a second stable condition at 40° C. and 75-100% relative humidity, with no visible water condensing on the interior surface of the window portion. The reservoir unit should be able to be moved swiftly between the two conditions, e.g. within 5 or 10 seconds. Further, the vent is adapted to provide 80% pressure equalization between the interior of the housing and the exterior at a pressure differential of 350 mBar in less than e.g. 60 or 30 minutes in order to assure proper working of pressure sensitive components. In this way it is possible to perform visual inspection of the reservoir at all times (e.g. also when the reservoir unit has just been removed from a refrigerator) without being confused by dew or condensed water drops. Such a situation of use would be relevant for a prefilled reservoir unit containing a drug which requires storage at a given low temperature as is the case for e.g. insulin-containing drugs. As the user in most cases would inspect the reservoir shortly after the reservoir has been moved between the two conditions, e.g. after the unit has been taken out of a refrigerator, the reservoir unit may be adapted to prevent visible water condensing on the interior surface of the window portion within a predetermined period of time, e.g. 5, 10 or 30 minutes.

Although "visible condensing" may appear to be a relative term, it is considered to be a well-defined condition readily recognizable by the average user, e.g. the formation of either larger droplets or visible dew which would both interfere with visual inspection of the interior of the reservoir through the window. As an example, when dew is forming on a glass surface, an area with dew is well limited against a surrounding area where no visible dew has formed, the transition between the two areas being readily identifiable by the average person.

In accordance with different embodiments of the present invention, the prevention of visible water condensing on the interior surface of the window portion can be achieved in a number of ways, e.g. the entrance of water in the housing can be delayed or prevented, or water having entered the housing may be prevented from condensing on the window.

A reservoir unit in which the vent is adapted to delay the entrance of aqueous vapour into the interior of the housing at a given aqueous pressure differential may for example comprise a membrane restricting the passage of aqueous vapour into the interior of the housing, e.g. in the form of a plug formed from a hydrophobic material, e.g. as supplied by Gore. The vent may also comprise a narrow conduit adapted to condense aqueous vapour as humid ambient air enters the interior of the housing, this preventing water from reaching components arranged deeper within the housing. The conduit may have any desired configuration, especially it does not have to be tubular but may have any cross-sectional configuration. Specifically, in the present context the term conduit also covers a relatively flat space between two substantially co-planar elements. To further aid in condensing water, the conduit may comprise a condensing portion serving as a heat sink. For example, a portion of the conduit may be arranged in the vicinity of either the reservoir or an electric energy source arranged within the housing, these two structures serving as "cold" reservoirs when the reservoir unit is moved from a colder to a warmer condition.

A reservoir unit in which the vent is adapted to prevent the entrance of aqueous vapour into the interior of the housing at a given aqueous pressure differential may for example comprise a valve controlled by the pressure differential between the interior of the housing and the exterior. In further embodiments the vent may comprise a molecular sieve in which water vapour will condense, or a capillary conduit adapted to condense aqueous vapour, the condensation of water blocking the conduit. The latter conduit may be combined with a heat sink as described above. To allow the vent to serve its pressure equalization purpose, the water condensed when the unit is moved from the first to the second stable condition should be allowed to evaporate within a relatively short time, e.g. in less than 30 minutes.

Correspondingly, in a preferred embodiment a pocket-sized reservoir unit is provided, comprising a housing defining an interior, the housing comprising a transparent window portion having an interior surface, a vent allowing ambient air and aqueous vapour to pass between the interior of the housing and the exterior, and a reservoir arranged within the interior of the housing, the reservoir defining an interior adapted to contain a fluid drug, the reservoir comprising a trans-parent portion allowing a user to inspect at least a portion of the contained drug through the transparent window portion and the transparent reservoir portion. The vent allows a flow of less than 7.5 l/h, preferably less than 5 l/h, more preferably less than 2.5 l/h, at a pressure differential of 500 mBar between the interior of the housing and the exterior. The pocket-sized unit may have a volume of less than 100 cm$^2$, preferably less than 50 cm$^2$.

In case aqueous vapour has entered the interior of the housing (or is allowed to enter the housing), it may be prevented from condensing on the interior surface of the window. For example, at least a portion of the space between the window portion and the transparent reservoir portion may be sealed thus preventing aqueous vapour to enter and potentially condense. In a further embodiment the interior surface of the window portion may be provided with a coating preventing condensation of water or preventing the visible condensation of water. The latter may be achieved by a microporous coating absorbing and distributing water over the surface. In a further embodiment a heating element is provided preventing condensation of water on the window portion, preferably arranged in the vicinity of the window.

In the above disclosure a number of individual solutions to the problem of avoiding condensation of water have been disclosed, however, two or more of the individual solutions may be implemented in combination in order to achieve the desired object of venting the housing and at the same protecting the window portion from condensation of water. Indeed, the disclosed solutions may also serve to control water condensation inside the housing in general, e.g. it may be desirable to prevent water condensation on electronic components. In addition to controlling entrance of aqueous vapour, the above described vent will also prevent fluids (e.g. water) and dust from entering the interior.

The reservoir may comprise first and second flexible foil portions sealed together to form an enclosed cavity for containing the fluid, the reservoir having a pouch-like configuration.

The reservoir unit may be provided with a fluid outlet and an expelling assembly adapted for co-operation with the reservoir to expel fluid drug out of the reservoir and through the fluid outlet. The term outlet is used to denote a structure which will serve as an outlet during actual delivery of drug. In other words, the outlet may be closed when not actually used. For example, the outlet may be in the form of a needle-penetratable septum which will be closed until a needle is arranged there through. The outlet may also be provided with a valve which will close the outlet until the delivery expelling means is actuated.

Such a unit may further comprise, or be adapted to cooperate with, a transcutaneous device (e.g. a needle, a soft cannula, a micro needle array, a traditional infusion set or non-invasive transdermal means, projecting from or arranged on a lower surface of a skin-mountable device in a situation of use). The unit may also comprise a mounting surface adapted for application to the skin of the subject, wherein the expelling assembly, in a situation of use, is adapted for expelling drug out of the reservoir and through the skin of the subject via the transcutaneous device.

In an embodiment of the invention a medical device is provided, comprising a transcutaneous device unit and a reservoir unit as described above, the transcutaneous device unit comprising a transcutaneous device and a mounting surface adapted for application to the skin of the subject, wherein the expelling assembly is adapted for cooperation with the reservoir to expel fluid drug out of the reservoir and through the skin of the subject via the transcutaneous device, and wherein the transcutaneous device unit and the reservoir unit are adapted to be secured to each other in a situation of use. The units may comprise coupling means allowing the units to be releasable secured to each other, and the coupling means may be user actuatable, e.g. comprising one or more elements to be manipulated in order to release the coupling.

The medical device may be adapted to allow inspection of the reservoir only when the reservoir unit is detached from the transcutaneous device unit.

As used herein, the term "drug" is meant to encompass any drug-containing flowable medicine capable of being passed through a delivery means such as a hollow needle or cannula in a controlled manner, such as a liquid, solution, gel or fine suspension. Representative drugs include pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein.

In the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Firstly, with reference to FIG. 1 an embodiment of a modular drug delivery device will be described. The delivery device is shown as an example of a type of device in which one or more aspects of the present invention advantageously may be implemented, however, aspects of the present invention may be used in combination with any relevant drug delivery device in which it is desirable to check a characteristic of the drug.

The transcutaneous device unit 2 comprises a transcutaneous device in the form of a needle and will thus in the following be termed a needle unit, however, it the context of the present invention, it represents any transcutaneous device that may be used for drug delivery.

Figure 1:
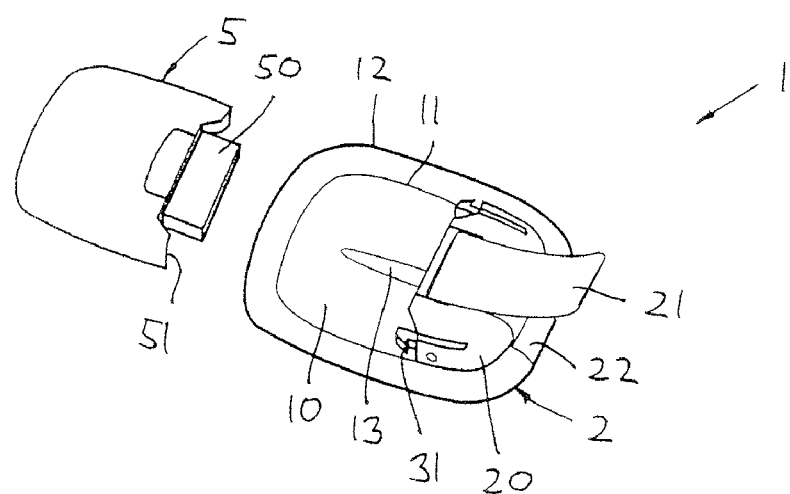
FIG. 1 shows in perspective view an embodiment of a modular drug delivery device.

More specifically, FIG. 1 shows a perspective view of medical device in the form of a modular skin-mountable drug delivery device 1 comprising a patch-like needle unit 2 and a reservoir unit 5. When supplied to the user each of the units are preferably enclosed in its own sealed package (not shown).

The needle unit comprises a base portion 10 with a lower mounting surface adapted for application to the skin of a user, and a housing portion 20 in which a hollow infusion needle (not shown) is arranged. The needle comprises a distal portion adapted to penetrate the skin of a user, and a proximal portion adapted to be arranged in fluid communication with the reservoir unit. The distal portion of the needle is moveable between an initial position in which the distal end is retracted relative to the mounting surface, and an extended position in which it projects relative to the mounting surface. Further, the needle is moveable between the extended position in which the distal end projects relative to the mounting surface, and a retracted position in which the distal end is retracted relative to the mounting surface. The needle unit further comprises user-gripable actuation means in the form of strip-members 21, 22 for actuating respectively retracting the needle. The housing further comprises user-actuatable male coupling means 40 in the form of a pair of resiliently arranged hook members adapted to cooperate with corresponding female coupling means on the reservoir unit, this allowing the reservoir unit to be releasable secured to the needle unit in the situation of use. The base portion comprises a relatively rigid upper portion 11 attached to a more flexible adhesive sheet member 12 having a lower adhesive surface providing the mounting surface per se, the adhesive surface being supplied with a peelable protective sheet. The base portion also comprises a ridge member 13 adapted to engage a corresponding groove on the reservoir unit.

The reservoir unit 5 comprises a pre-filled reservoir containing a liquid drug formulation (e.g. insulin) and expelling means in the form of an electronically controlled pump for expelling the drug from the reservoir through the needle in a situation of use. The reservoir unit has a generally flat lower surface adapted to be mounted onto the upper surface of the base portion, and comprises a protruding portion 50 adapted to be received in a corresponding cavity of the housing portion 20 as well as female coupling means 51 adapted to engage the corresponding hook members 31 on the needle unit. The protruding portion provides the interface between the two units and comprises a pump outlet and contact means (not shown) allowing the pump to be started as the two units are assembled. The lower surface also comprises a window (not to be seen) allowing the user to visually control the contents of the reservoir, however, such a window may also be arranged on an upper free surface of the reservoir unit.

Figure 2:
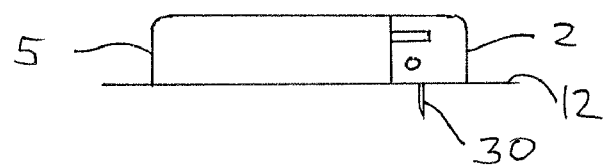
FIG. 2 shows a side view of an assembled drug delivery device.

FIG. 2 shows the reservoir and needle units in an assembled state with a needle 30 protruding from the lower surface thereof.

Figure 3:
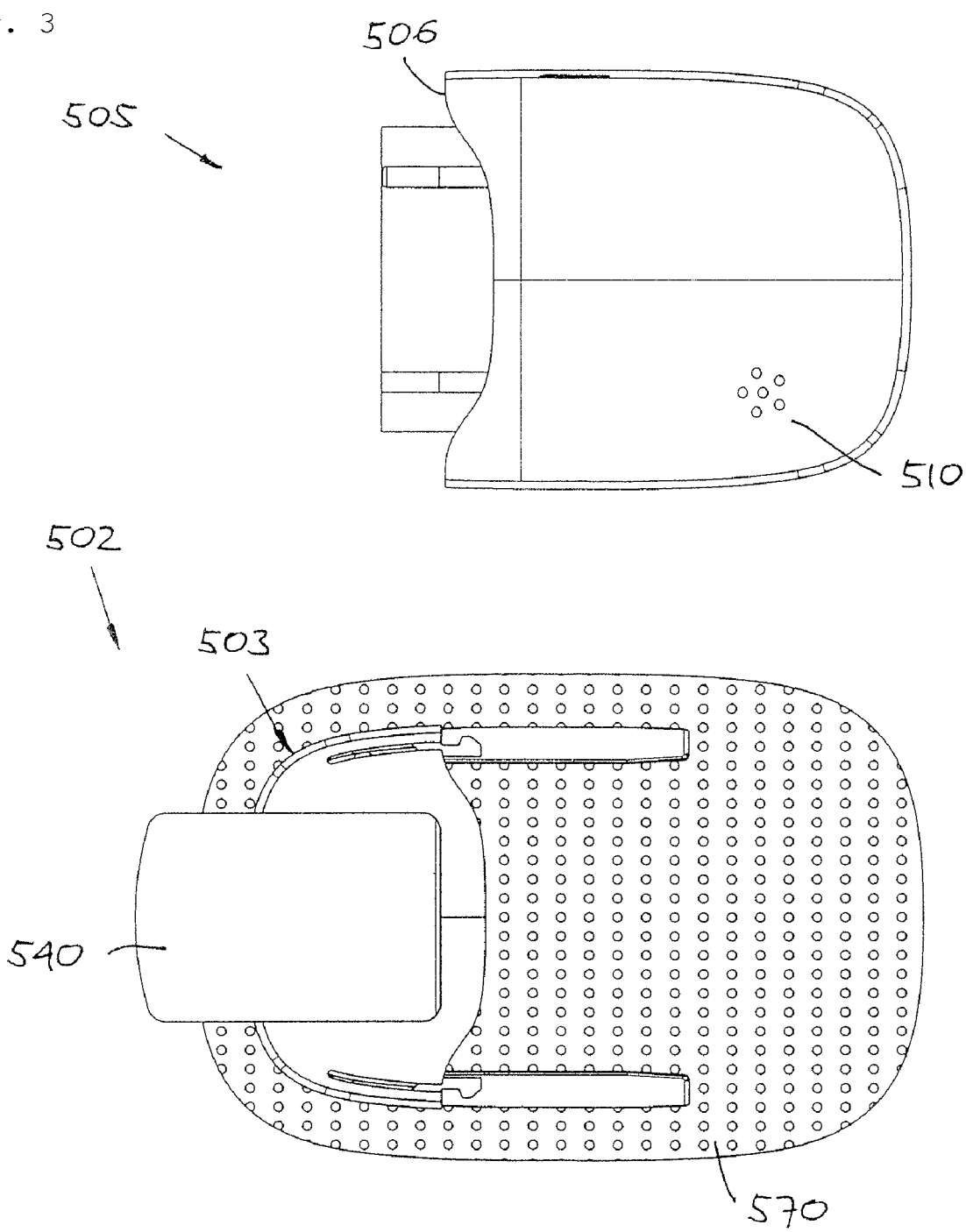
FIG. 3 shows in a non-assembled state a needle unit and a reservoir unit for a further embodiment of a drug delivery device.

FIG. 3 shows a further embodiment of medical device 500 substantially corresponding to the embodiment of FIG. 1, the device comprising a patch-like needle unit 502 and a thereto attachable reservoir unit 505 having a vent 510.

Figure 4:
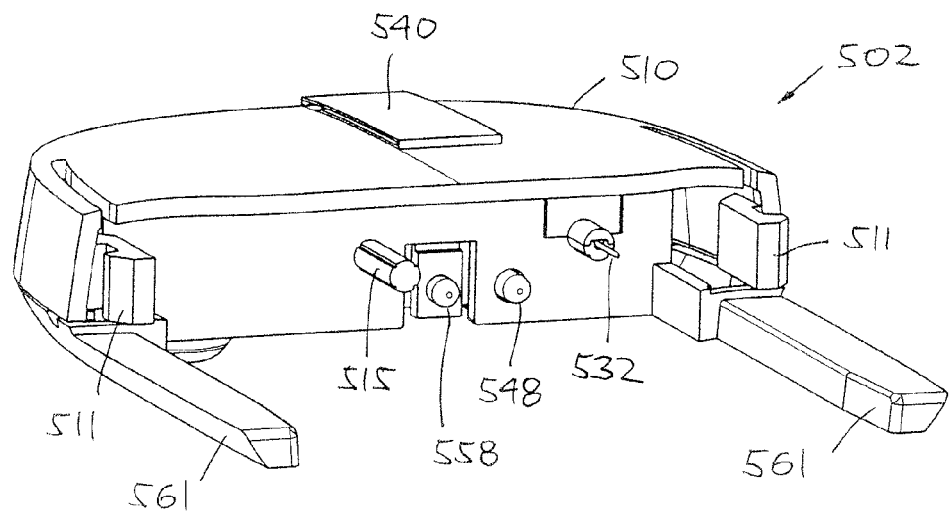
FIG. 4 shows a further perspective view of the needle unit of FIG. 3.

In FIG. 4 the side of the needle unit 502 which connects to the reservoir unit is shown. In addition to the two ridge members 561 and the user actuatable coupling means 511 the needle unit comprises further structures which connects to and/or engages the reservoir unit to provide a functional interface with the reservoir unit. More specifically, the needle unit comprises a fluid inlet provided by the pointed proximal portion 532 of the needle projecting from the needle unit and adapted to engage a fluid outlet of the reservoir unit, an actuator 515 projecting from the needle unit and adapted to engage and actuate a fluid connector in the reservoir unit (i.e. providing fluid communication between the pump and the reservoir), and first and second contact actuators 548, 558 adapted to engage corresponding contacts on the reservoir unit. The first contact actuator is provided by a portion of the needle actuator projecting through an opening in the housing, and the second contact actuator is provided by a hinged portion of the housing connected to a needle retraction member. When the needle unit is first connected to the reservoir unit both contact actuators will protrude from the housing and engage the corresponding contacts on the reservoir unit thereby indicating that that a needle unit has been connected. When the needle is actuated the first contact actuator will be withdrawn and thereby disengage the corresponding contact on the reservoir unit to start pump actuation. When the needle is retracted the second contact actuator will pivot and disengage the corresponding contact on the reservoir unit to stop pump actuation. Indeed, the interface between the two units may be configured in many different ways and may provide different functionalities. For example, the system may be intended for placement and actuation of the needle before the reservoir unit is connected.

Figure 5:
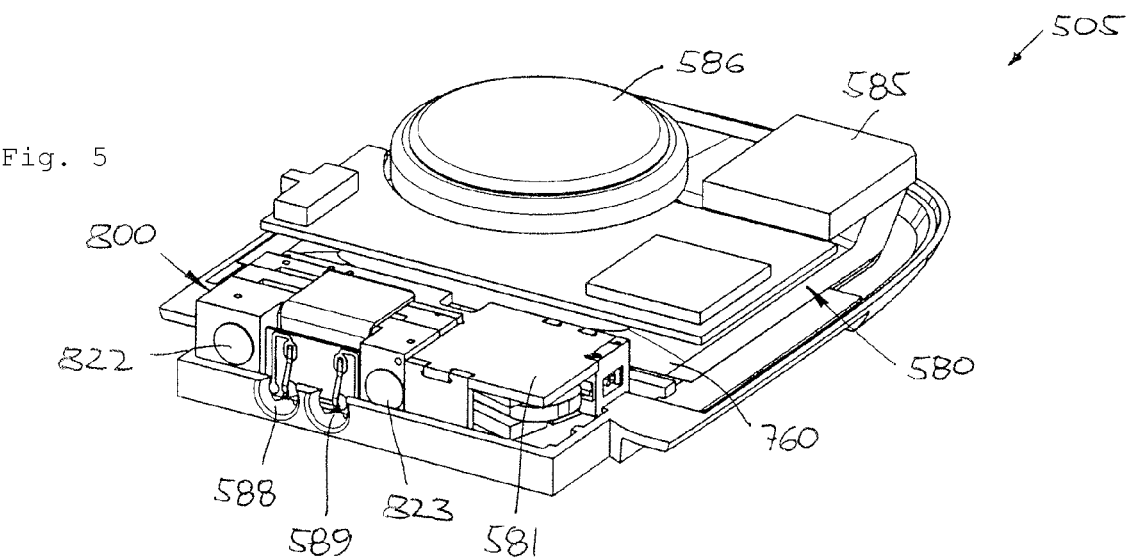
FIG. 5 shows a perspective view of the interior of the reservoir unit of FIG. 3.

FIG. 5 shows the reservoir unit with an upper portion of the housing removed. The reservoir unit comprises a reservoir 760 and an expelling assembly comprising a pump assembly 800 and control and actuation means 580, 581 therefore. The pump assembly comprises an outlet 822 for connection to a transcutaneous access device (e.g. the needle xxx) and an opening 823 allowing the internal fluid connector to be actuated. The reservoir 560 is in the form of prefilled, flexible and collapsible pouch comprising a needle-penetratable septum adapted to be arranged in fluid communication with the pump assembly. The shown pump assembly is a mechanically actuated membrane pump, however, the reservoir and expelling means may be of any suitable configuration. The control and actuation means comprises a pump actuating member in the form of a coil actuator 581 arranged to actuate a piston of the membrane pump, a PCB or flex-print to which are connected a microprocessor 583 for controlling, among other, the pump actuation, contacts 588, 589 cooperating with the contact actuators on the needle unit, signal generating means 585 for generating an audible and/or tactile signal, an optional display (not shown) and an energy source 586. The contacts are preferably protected by membranes which may be formed by flexible portions of the housing. The reservoir unit may further be provided with receiving and transmission means allowing the unit to be controlled wirelessly by a remote controller.

Figure 6:
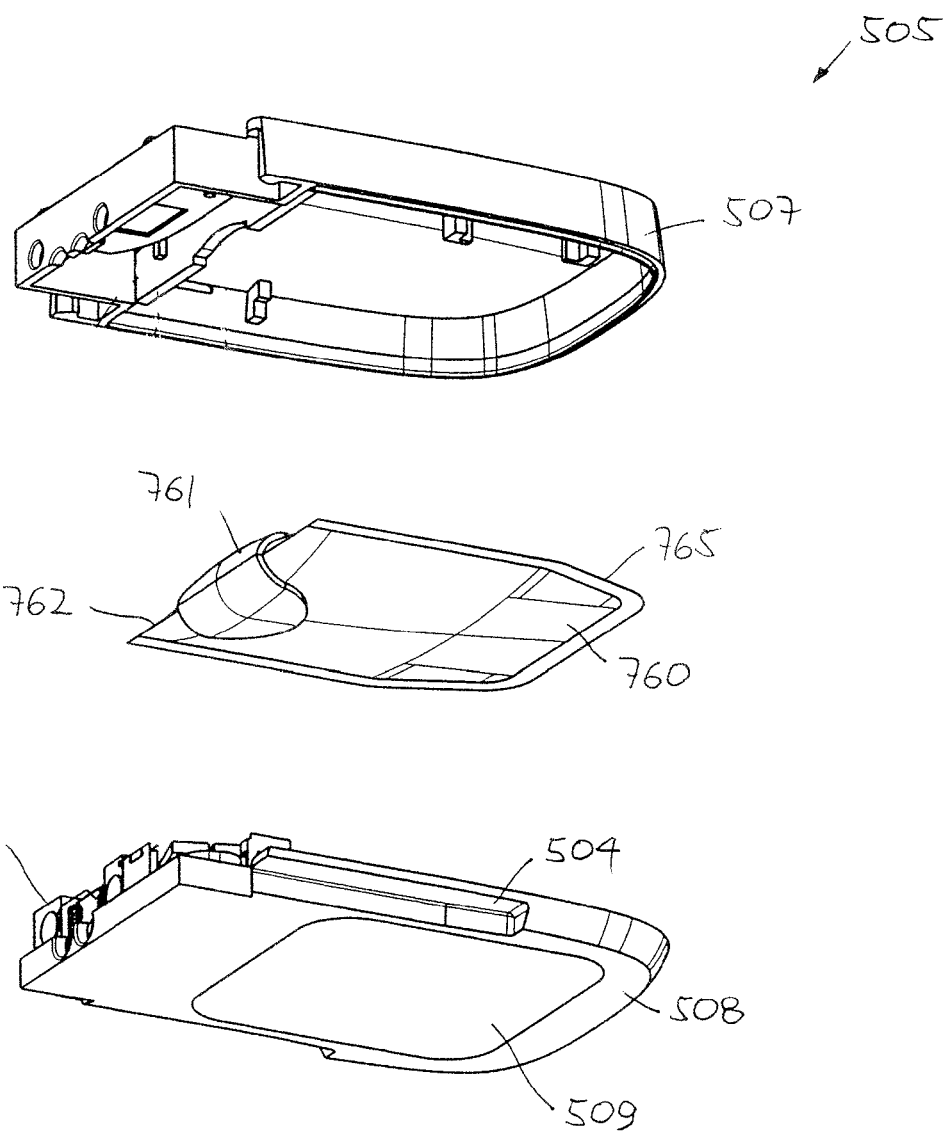
FIG. 6 shows an exploded view of a further reservoir unit.

In FIG. 6 an exploded view of the reservoir unit 505 of FIG. 3 is shown, the unit comprising an upper housing member 507, a lower housing member 508 with a transparent area 509 and grooves 504 to receive the ridge members 561 extending from the needle unit, a flexible reservoir 760 with a rounded edge portion 762 on which a septum member 761 is mounted, a pump assembly 800 with actuator and a circuit board (not shown) arranged above the reservoir and comprising electronic components for controlling actuation of the pump.

Further details and embodiments in respect of a modular drug delivery device of the type shown in FIGS. 1-6 are disclosed in applicant's WO 2005/039673 which is hereby incorporated in its entirety by reference.

With reference to schematic FIGS. 7A-7D four embodiments of a reservoir unit comprising means to prevent visible water condensing on the interior surface of a window portion of reservoir unit is shown. The reservoir units are of the type disclosed with reference to FIGS. 1-6, however, for illustrative purposes only the elements necessary to illustrate the central aspects of the different embodiments are shown.

Figure 7A:
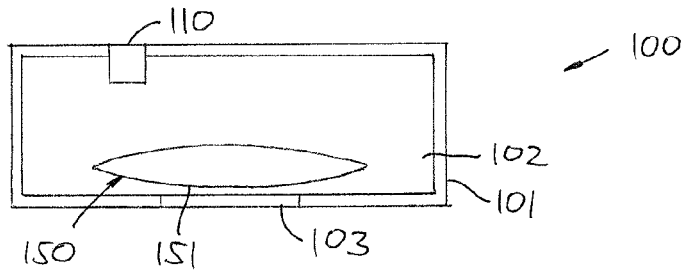
FIGS. 7A-7D show embodiments of a reservoir unit comprising means to prevent water condensing.

More specifically, FIG. 7A shows a reservoir unit 100 comprising a housing 101 defining an interior 102, the housing comprising a transparent window portion 103 having an interior surface. A reservoir 150 is arranged within the interior of the housing, the reservoir defining an interior adapted to contain a fluid drug, the reservoir comprising a transparent portion 151 allowing a user to inspect at least a portion of the contained drug through the transparent window portion and the transparent reservoir portion. The shown reservoir comprises first and second flexible foil portions sealed together to form an enclosed cavity for containing the fluid, the reservoir having a pouch-like configuration, however, the reservoir may have any desirable configuration. A venting element in the form of a vent plug 110 is provided allowing ambient air and aqueous vapour to pass between the interior of the housing and the exterior. The plug in combination with the remaining properties of the reservoir unit assures that 80% pressure equalization between the interior of the housing and the exterior at a pressure differential of 350 mBar is provided in less than 30 minutes when the plug is not blocked, see below. At the same time the plug controls influx of water vapour such that the reservoir unit is adapted to be moved from a first stable condition at 5° C. and 0-100% RH, to a second stable condition at 40° C. and 75-100% RH within a period of time of less than 5 seconds, with no visible water condensing on the interior surface of the window portion.

The vent plug may be of a type restricting the passage of aqueous vapour, e.g. a hydrophobic plug element of the type supplied by Gore. The actual properties for a plug providing the desired functionality for a given reservoir unit will depend on a number of factors such as the physical properties of the reservoir unit (e.g. size, materials, spatial arrangement of components inside the housing) as well as other means provided serving to limit condensation of water. For a prototype embodying principles of the present invention the Gore membranes D3TV 911935 and D3TV 911938 were found to work satisfactiously.

Alternatively the vent plug 110 may be of a type preventing the passage of aqueous vapour by allowing the vapour to condense within the plug. For example, the plug may comprise a so-called molecule sieve which is a micro-porous structure in which the water molecules will be withhold at first but is subsequently allowed to evaporate at a later time when the plug has achieved a higher temperature. If the vapour load is high the full venting potential of the plug may be diminished until it has dried. In a further alternative the vent plug may comprise a valve controlled by the pressure differential between the interior of the housing and the exterior. For example, the valve may be a passive valve adapted to open at a given pressure differential (e.g. 50 mBar) which for a given pump has been found not to interfere with the functionality of the reservoir unit. Indeed, such a solution would be based on the assumption that a sudden change of both the pressure differential and the temperature differential between the interior of the housing and the exterior is unlikely.

Figure 7B:
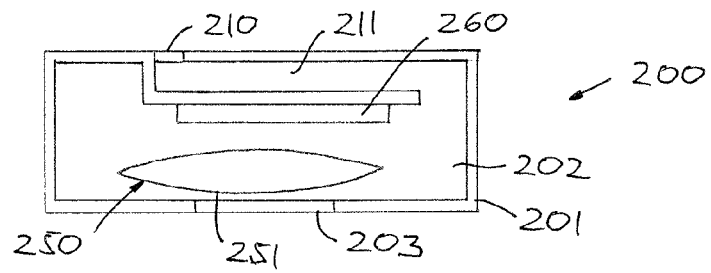

In FIG. 7B is shown a reservoir unit 200 of the same general type as in FIG. 7A comprising a housing 201 with a vent opening 210, a transparent window portion 203, and a reservoir 250. A venting element in the form of a conduit 211 is provided between the vent opening and the interior 202 of the housing. The vent conduit may be of a type restricting the passage of aqueous vapour by allowing at least a portion of the vapour to condense within the conduit without blocking the passage of air. Alternatively, the vent comprises a capillary conduit adapted to condense aqueous vapour, the condensation of water blocking the conduit until the condensed water has evaporated.

Both types of conduits may be combined with a heat sink 260 which will serve to further reduce the temperature of the incoming vapour, thus accelerating condensation of water. For example, in a given reservoir unit further comprising a pump assembly and an energy source in the form of an electric cell (or "battery"), the reservoir and/or the electric cell would have a relatively large heat storage capacity that would keep a low temperature for a longer time than some of the other components of the reservoir unit. In exemplary embodiments a surface portion of the heat sink, e.g. the relatively large and substantially planar outer surfaces of a 3V lithium cell, may form a portion of the conduit.

Figure 7C:
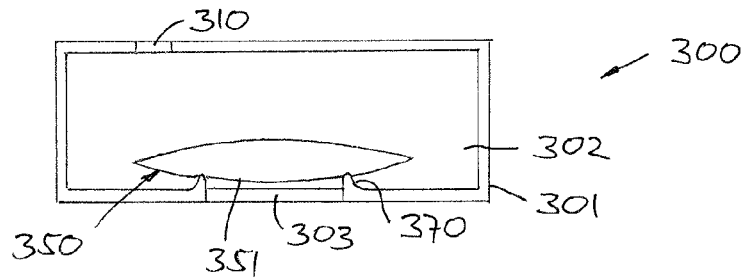

In FIG. 7C is shown a reservoir unit 300 of the same general type as in FIG. 7A comprising a housing 301 with a vent opening 310, a transparent window portion 303, and a reservoir 350. To prevent aqueous vapour from entering the space between the reservoir and the window portion and subsequently condense on the interior surface of the window when the reservoir unit is transferred between the first and second conditions, a seal 370 is arranged between the reservoir and the window portion, the seal preventing vapour from entering the space. The seal may be in the form of a separate seal element (e.g. an O-ring) or it may be formed integrally with the housing as shown. As the problem of condensation is primarily associated with the step of taking a new reservoir unit out of cold storage, the seal may be adapted to only engage a form-changing reservoir (e.g. a flexible pouch reservoir) in its fully filled condition.

Figure 7D:
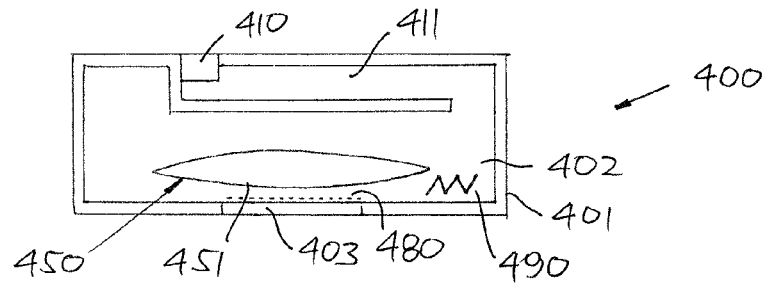

In FIG. 7D is shown a reservoir unit 400 of the same general type as in FIG. 7A comprising a housing 401 with a vent opening 410, a transparent window portion 403, and a reservoir 450. To prevent aqueous vapour to condense on the interior surface of the window portion when the reservoir unit is transferred between the first and second conditions, the inner surface of the window portion is provided with a coating 480 preventing condensation of water or preventing the visible condensation of water. To further assist in the prevention of condensation of water on the window, a heating element 490 (requiring an energy source, not shown) is provided in the vicinity of the window. To illustrate that the different features described above to prevent condensation of water on the window can be used in combination, the embodiment of FIG. 7D further comprises a vent plug 410 and a conduit 411.

In the following two examples the difference in properties between an embodiment of the present invention and a conventional infusion pump will be illustrated.

EXAMPLE 1

Scope of the test: Condensation effects on the inspection window.

Test object: 15 reservoir units of the same general design as in FIGS. 6 and 7, i.e. comprising a reservoir and an inspection window, the remaining components being replaced with dummy components having representative properties for heat storage. All units were mounted with 2K Gore membranes having allowing a flow of 1.2 l/h at a pressure differential of 500 mBar between the interior of the housing and ambient air.

Test object is to be moved from hot and humid place (T=+40° C., RH=98%) into a cold and semi humid place (T=+5° C., RH=75%) for nine cycles lapsing over three days. Two climate champers are used: Cl_hot; T=+40° C., RH=98%, and Cl_cold; T=+5° C., RH=75%

Test cycle: (1) Start of cycle, (2) specimens are placed in Cl_cold for 60 min., (3) specimens are placed in Cl_hot for 60 min., (4) condensation effects on the inside of the inspection window are observed, and (5) end of cycle, go to step 2—if three cycles has been performed leave specimens in Cl_hot for the night; go to step 1 next morning.

Moisture observations: Tests was performed according to schedule presented above with 9 cycles (3 per day). No moisture was observed during the 3 days.

Conclusions: As no moisture is observed, this test provides an early indication that the water protection concept is OK. It is shown that a pump units fitted with a 2K membrane, exposed to shifting temperatures (between 5° C. and 40° C.) and a relative high humidity (98% RH), to a sufficient degree can prevent condensation inside the pump unit.

EXAMPLE 2

Scope of the test: To clarify if condensation effects appear on the inside of the inspection window in a regular insulin pump.

Test object: One MiniMed Paradigm® pump with catheter applied has been tested. The pump comprises an inspection window through which a cartridge can be inspected. The pump is mounted with a membrane having allowing a flow of 15.2 l/h at a pressure differential of 500 mBar between the interior of the pump housing and ambient air.

The test procedure: Test object is to be moved from hot and humid (T=+40° C., RH=98%) into a cold and semi humid place (T=+5° C., RH=75%) for a total of nine cycles lapsing over three days. Between each move the pump is inspected for a few minutes at 20° C. and 75% RH.

Procedure for each cycle: (1) Start of cycle, (2) the specimen is placed in cold environment for approximately 60 min, (3) specimen is observed for ½-3 minutes; photos are taken if dough is experienced, (4) specimen is placed in hot environment for approximately 60 min, (5) specimen is observed for ½-3 minutes; photos are taken if dough is experienced, and (6) end of cycle. At each observation point the outside of inspection window is cleaned from condensate.

Results: During the three days of testing, dough was experienced from the beginning of the $2^{nd}$ day (or from the $4^{th}$ cycle). The dough is situated on the window area near the ventilation membrane and fills an area of approximately 10-20 mm$^2$. During the $3^{rd}$ day the dough intensity was increasing during the day. In the observation environment of 20° C. and 75% RH the dough is visible for a period of 1-3 minutes where after it begins for evaporate. After another 1-3 minutes the dough is finally gone.

Conclusions: Dough between the inspection window and the insulin reservoir is experienced when a pump in a hot and humid environment, e.g. in Asia (Temp=+40° C., RH=98%) is stored in a cooler 3 times over 3 days.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A method of preventing condensate on an interior window portion contained in a housing in a reservoir unit for an insulin pump device, wherein the window allows a user to inspect the drug contained in the reservoir, the method comprising the steps of:

placing the reservoir unit in a refrigerator and allowing it to reach a first stable condition having a first temperature and humidity;

removing the reservoir unit from the refrigerator and placing it in an environment with a second temperature and humidity, wherein the second temperature is higher than the first temperature;

venting an interior portion of housing to the ambient air; wherein the venting allows an 80% pressure equalization between the interior of the housing and the exterior at a pressure differential of 350 mBar in less than 60 minutes and wherein the venting allows ambient aqueous vapour to pass from the exterior to the interior of the reservoir unit; and preventing visible water condensation from forming on the interior surface of the window portion.

* * * * *